(12) United States Patent
Ritchie et al.

(10) Patent No.: US 12,011,342 B2
(45) Date of Patent: Jun. 18, 2024

(54) ATRAUMATIC BANDAGE/DRESSING TO COVER WOUND, SURGICAL INCISION, EPIDERMAL MEDICAL DEVICE, OR NON-MEDICAL APPLICATION

(71) Applicants: William James Ritchie, McGaheysville, VA (US); Walter James Ferguson, Sebastian, FL (US)

(72) Inventors: William James Ritchie, McGaheysville, VA (US); Walter James Ferguson, Sebastian, FL (US)

( * ) Notice: Subject to any disclaimer, the term of this patent is extended or adjusted under 35 U.S.C. 154(b) by 320 days.

(21) Appl. No.: 17/703,055

(22) Filed: Mar. 24, 2022

(65) Prior Publication Data

US 2022/0313495 A1     Oct. 6, 2022

Related U.S. Application Data

(60) Provisional application No. 63/167,701, filed on Mar. 30, 2021.

(51) Int. Cl.
| | | |
|---|---|---|
| *A61F 13/02* | (2024.01) | |
| *A61F 13/00* | (2024.01) | |
| *A61F 13/0246* | (2024.01) | |

(52) U.S. Cl.
CPC ...... *A61F 13/0289* (2013.01); *A61F 13/0253* (2013.01); *A61F 2013/00182* (2013.01)

(58) Field of Classification Search
CPC .............. A61F 13/0289; A61F 13/0253; A61F 2013/00182; A61F 13/00051; A61F 13/023; A61F 13/00; A61F 13/02; A61F 13/0276
See application file for complete search history.

(56) References Cited

U.S. PATENT DOCUMENTS

| | | | |
|---|---|---|---|
| 4,526,166 A | 7/1985 | Silber | |
| 5,951,505 A | 9/1999 | Gilman et al. | |
| 8,362,315 B2 * | 1/2013 | Aali | A61F 15/002 604/289 |
| 8,403,899 B2 * | 3/2013 | Sherman | A61F 13/023 602/41 |
| 2013/0310725 A1 | 11/2013 | Jerrells et al. | |
| 2016/0206479 A1 | 7/2016 | Montulet | |
| 2021/0161720 A1 * | 6/2021 | Kantrowitz | A61M 5/14248 |

\* cited by examiner

*Primary Examiner* — Tarla R Patel

(57) ABSTRACT

Dressing or bandage for protecting a wound accidentally incurred, surgical incision deliberately made in the skin, epidermal delivery of medication, or musculotherapy of a human being or animal, said bandage/dressing having the primary characteristic of being significantly atraumatic upon removal of same by virtue of a novel stringlike member that is intentionally incorporated into or debossed into the construction of said parent bandage/dressing in a multi-spiral geometry, said stringlike member firstly being pulled gently and progressively in multiple turns around the wound site or epidermal treatment area to in effect significantly reduce the area of remaining/undisturbed adhesive between the bandage/dressing and patient's skin before the bandage/dressing is peeled away from the skin in conventional manner and thus affording the patient a significantly less traumatic experience.

13 Claims, 7 Drawing Sheets

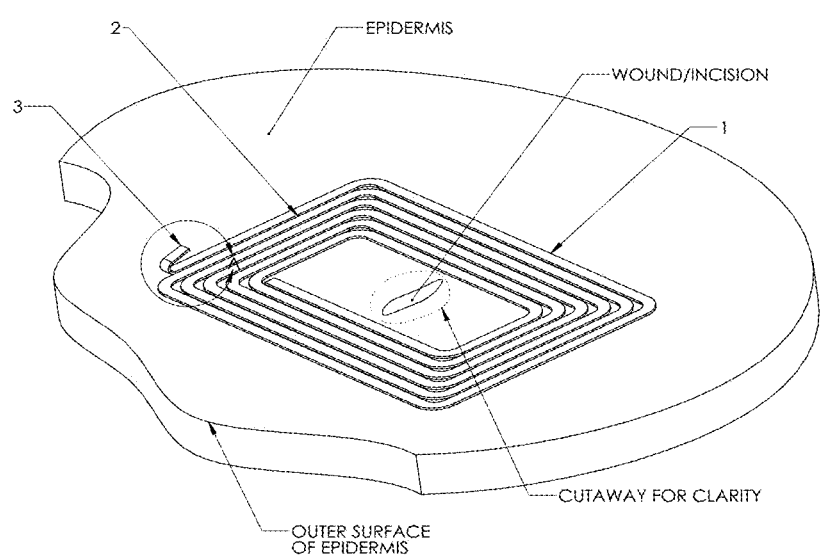
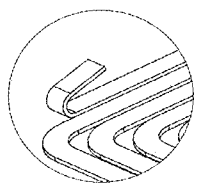
FIG. 6B
FIG. 6A
FIG. 6

Detail A

ATRAUMATIC BANDAGE/DRESSING TO COVER WOUND, SURGICAL INCISION, EPIDERMAL MEDICAL DEVICE, OR NON-MEDICAL APPLICATION

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

It is well known how traumatic to a patient the removal of a bandage/dressing from the patient's skin can be. This is particularly true of patients requiring large surface areas dressings associated with epidermal sports bandages, nicotine patches, insulin pump applications, periodic intravenous treatment, or chemotherapy infusions in the field of oncology. Whether it is a PIC line or a 'port-a-cath,' the dressing covering the site of the entrance to the catheter invariably requires a dressing of relatively large area, as compared to one that would be employed for a minor cut, to ensure that the PIC line or 'port-a-cath' remains firmly in place and that no bacteria-causing infection can migrate from the ambient to the catheter. The removal of this relatively large, dressing area is primarily responsible for the felt trauma upon dressing removal.

The required force to remove a dressing is proportional to the value of adhered area, in square inches, for example. Compounding the patient's trauma, in these particular dressings a relatively high strength adhesive is generally employed. The patient's typical trauma may be said to be caused by both the quantitative value of the covered wound area and the type of adhesive/bonding agent inherent to this kind of dressing. Further adding to the patient's misery, these particular adhesives are so aggressive in terms of strength, noxious solvents such as acetone are generally applied to the topical area after the dressing has been removed, and this only to rid the patient's skin of the adhesive residue. It should also be noted that oncology patients suffer the necessity of multiple, repeated treatments or sessions, hence an accumulation of patient trauma over time.

The prior art includes US20130310725A1 which teaches the incorporation of a pull string said action upon only breaks a multiplicity of tiny pouches or cells containing acetone or the like to weaken the bond strength of the adhesive. While the goal of this present application may have been anticipated by US20130310725A1, the need for the noxious solvents and their detrimental effect on the patient had not hitherto been eliminated.

In U.S. Pat. No. 5,951,505A one sees a pull tab embedded in the bandage/dressing but employed only for the purpose of aiding the application of the bandage/dressing to the wound site, not its removal.

In US2016/0206479 A1 Montulet "Easy Removal Adhesive Article" one sees the incorporation of a pair of parallel die cuts for removal of a specific single-wrap, band application, but not in multi-turn, spiral, stringlike geometry, and not positioned to aid in large surface article removal as envisioned and claimed in this disclosure.

In US1985/4526166A Silber one sees die cut strips, that serve as a bridge between wound site gauze and adhesive portion of the bandage but not in multi-turn, spiral, stringlike geometry, and not positioned to aid in large adhesive surface article removal as envisioned and claimed in this disclosure.

BRIEF SUMMARY OF THE INVENTION

The novel bandage/dressing construction contained here within seeks to significantly ameliorate these patient traumas by primarily incorporating or mimicking a stringlike member which the caregiver can gently unwind, thus greatly lowering the required, externally applied peel force and hence pain/trauma perceived by the patient during final removal of the dressing. The second benefit to the patient when the novel construction herein is employed is ideally the complete lack of need for the aforementioned solvents traditionally employed in bandages/dressings found in the prior art, since such small surface area associated with spiraling, stringlike applications have incrementally lower pull force and proportionately associated less pain upon removal.

BRIEF DESCRIPTION OF THE SEVERAL VIEWS OF THE DRAWING

FIG. 6—Illustration of fourth and preferred embodiment whereby debossed or perforated dressing to mimic stringlike spiral geometry to facilitate easy removal.

DETAILED DESCRIPTION OF THE INVENTION

Figure 1:
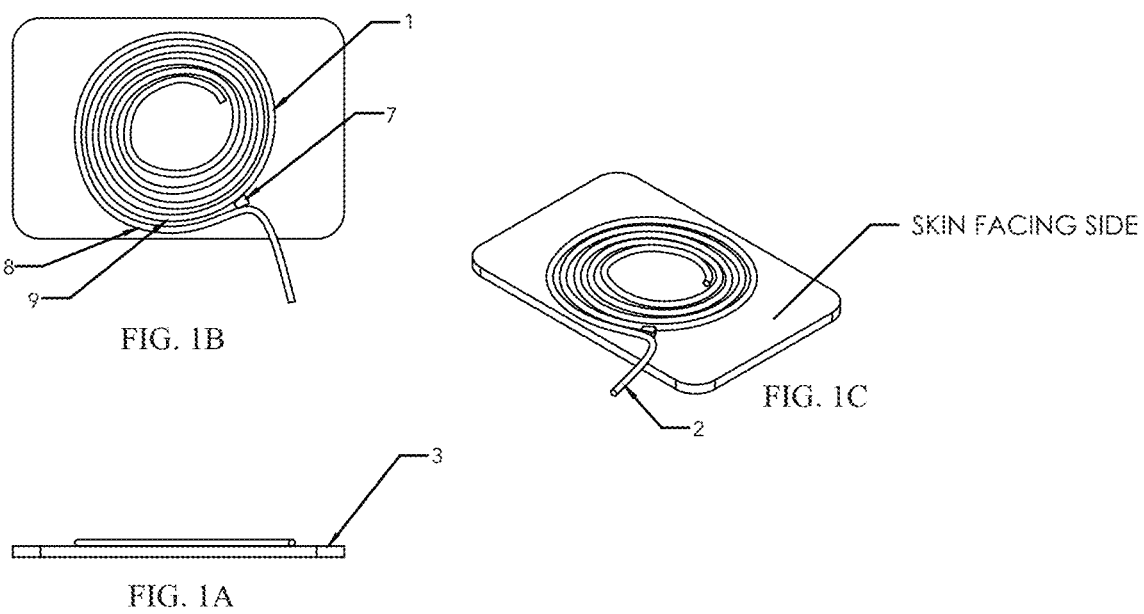
FIG. 1—Illustration of first embodiment of improved dressing depicting spiral bands of stringlike feature.

In a first embodiment FIG. 1 shows the improved dressing, which is the subject of this application, in position ready to be put down over the patient's wound, incision or port site. Stringlike member 1 is attached to the body proper of bandage/dressing 3 in FIG. 1A and features tail 2 in FIG. 1C protruding from the edge of bandage/dressing 3. Stringlike member 1 in FIG. 1B may be inelastic, elastic porous or non-porous.

Stringlike member 1 with tail 2, which may be thought of as being akin to commercially available dental floss, is laid down over the skinfacing side of bandage/dressing 3 at time of manufacture and of a predetermined coil shape in members 8 and 9 in FIG. 1B. The string shape in in FIG. 1B may be in the form of an Archimedean spiral but other multi-turn geometries are envisioned within the scope of this disclosure—notably triangular spiral, square spiral, rectangular spiral, hexagonal spiral, octagonal spiral and even irregularly spaced spiral. Stringlike member 2 may be held in place by the bandage's adhesive. The inclusion of one small patch of gel/adhesive 7 in FIG. 1B may be intentionally laid down between outermost turn 8 and its adjacent turn 9 of stringlike member 1 and at the exterior edge of dressing 3, outermost turn emanating from tail 2 in FIG. 1C of said stringlike member. Patch 7 is only required if there is a space deliberately employed between turns 8 and 9 of stringlike member 1 in FIG. 1B when it is laid down onto the skin facing side of dressing 3 in FIG. 1C at time of manufacture. If on the other hand there is virtually no space between the outermost turn and its adjacent turn, then patch 7 is not required. In any event, employment of patch 7 constitutes a higher level of assurance that the wound/incision/port side once covered with this improved dressing will not be subject to bacterial infection while the wound heals or between oncology treatment sessions.

Figures 2, 2A:
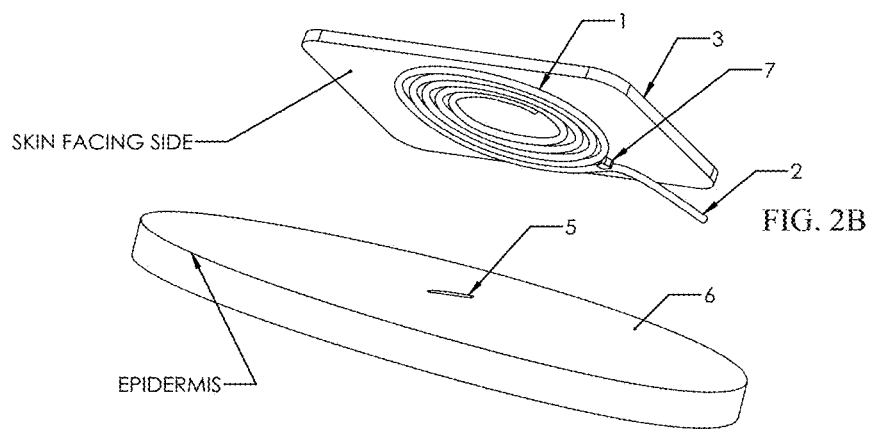
FIG. 2—Illustration of improved dressing in relation to application on skin surface.
Figure 3:
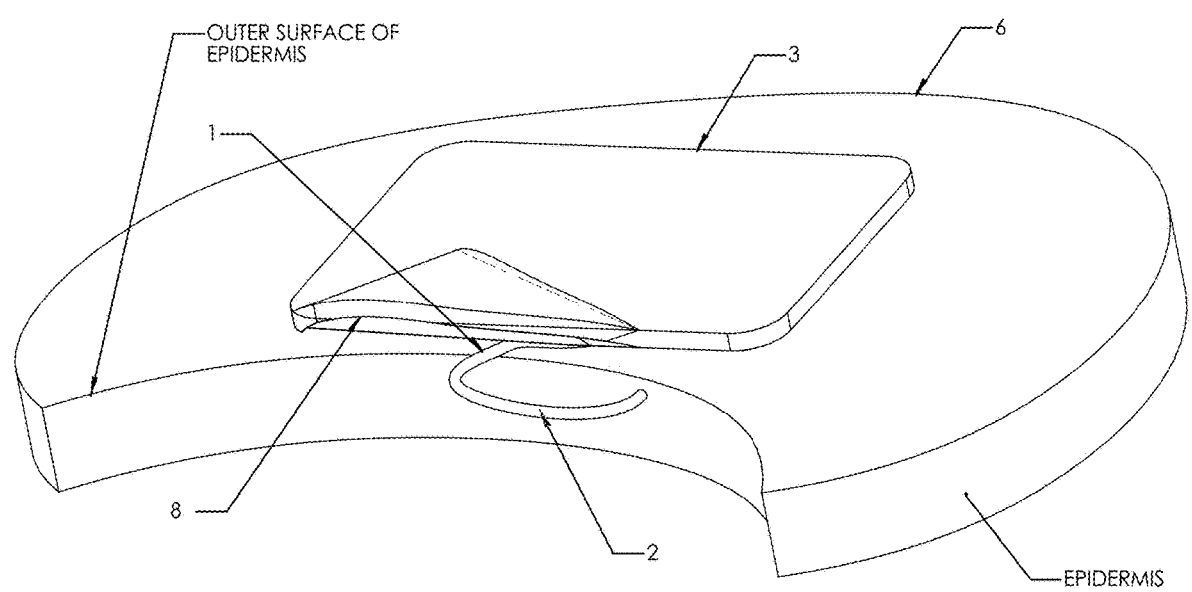
FIG. 3—Illustration of whereby stringlike feature carrying all adhesives for adherence to the skin and dressing.

FIG. 2 shows the improved dressing in its state of being at time of application to the patient. The receiving wound/incision site 5 in FIG. 2A is shown on patient's epidermis 6 in FIG. 2A. Wound/incision site 5 in FIG. 2A could also be an oncology port (not shown). Tail 2 in FIG. 2B is shown protruding sufficiently to be gripped by a human hand but not yet having been touched or disturbed. With reference to FIG. 3 and when the time has come to remove subject dressing in whole from the patient's skin the care giver, or patient himself, simply pulls on the tail 2 in FIG. 3 in a steady, gentle, unwinding motion—preferably the dressing is manufactured so that this unwinding will be in an intuitively counter-clockwise fashion. This motion causes the leading edge of bandage 3 in FIG. 3 to form, gradually increasing in size, pucker 8 in FIG. 3, thus beginning the cascading process of the stringlike member 2 generally defeating what otherwise would be the relatively high bond strength of the dressing to the skin. Once the string has been fully removed, much less force will be needed to remove the dressing/bandage from the patient's skin and the associated trauma the patient experiences in this process will be significantly and proportionately reduced to his/her benefit.

In the course of manufacture of the improved bandage/dressing revealed herein stringlike member 1 in FIG. 3 is firstly coated with an appropriate gel/adhesive which will give it mechanical adherence in sufficient degree to both dressing body 3 and the patient's skin 6 when laid in place on the body of the dressing and later when affixed to the patient's skin. This same gel/adhesive provides the necessary seal to the skinfacing surface of the dressing as well as to the patient's skin to fully preclude bacteria passing by to wound/incision site 5 in FIG. 2 and subsequent infection at the wound site.

Figure 4:
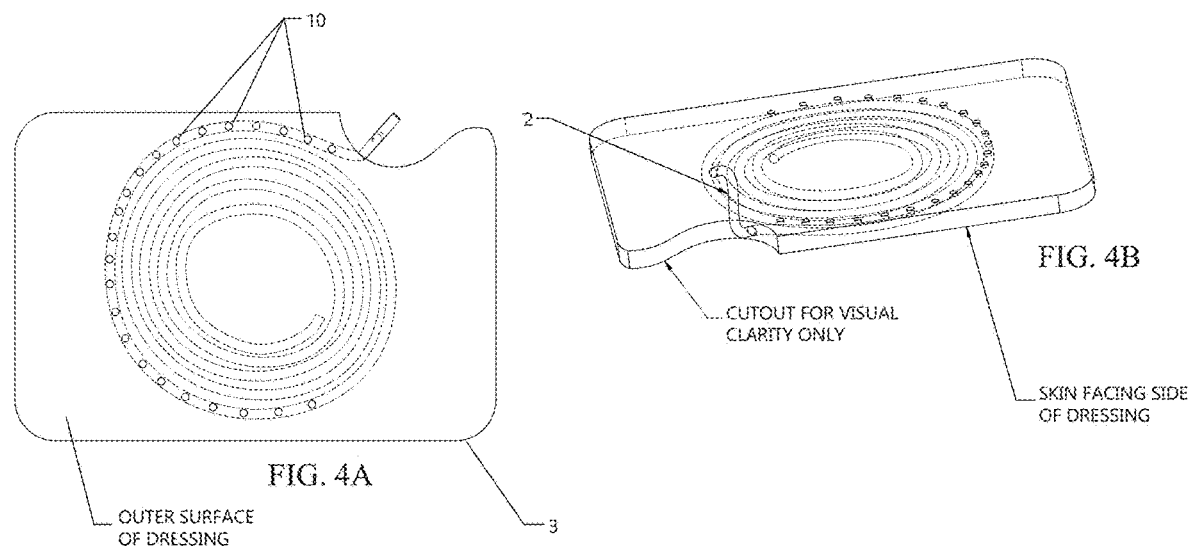
FIG. 4—Illustration of second embodiment whereby stringlike member is embedded within dressing/bandage which includes a multitude of perforations that facilitate removal.

With reference to FIG. 4A a second embodiment is presented whereby the stringlike member is embedded within dressing/bandage 3 in the latter of which includes a multitude of perforations 10 in FIG. 4A that facilitate removal of stringlike member when tail 2 in FIG. 4B is pulled in a direction generally away from the patient's skin as opposed to pulling tail 2 in FIG. 2B tangentially as seen in the first embodiment. In FIG. 4 the inclusion of perforations 10 in FIG. 4A in the manufacture of the complete article allows, through a cascading effect, tail 2 in FIG. 4B to be pulled away from the patient's skin. As perforations 10 are clearly visible at the time of removing the dressing/bandage from the patient's skin the desired action to avoid trauma in removing the dressing/bandage from the patient is more intuitive. As in the previous embodiment once the string has been removed much less force and trauma will be needed to remove the dressing/bandage from the patient's skin and again without resort to noxious solvents to remove residual adherent.

Figure 5:
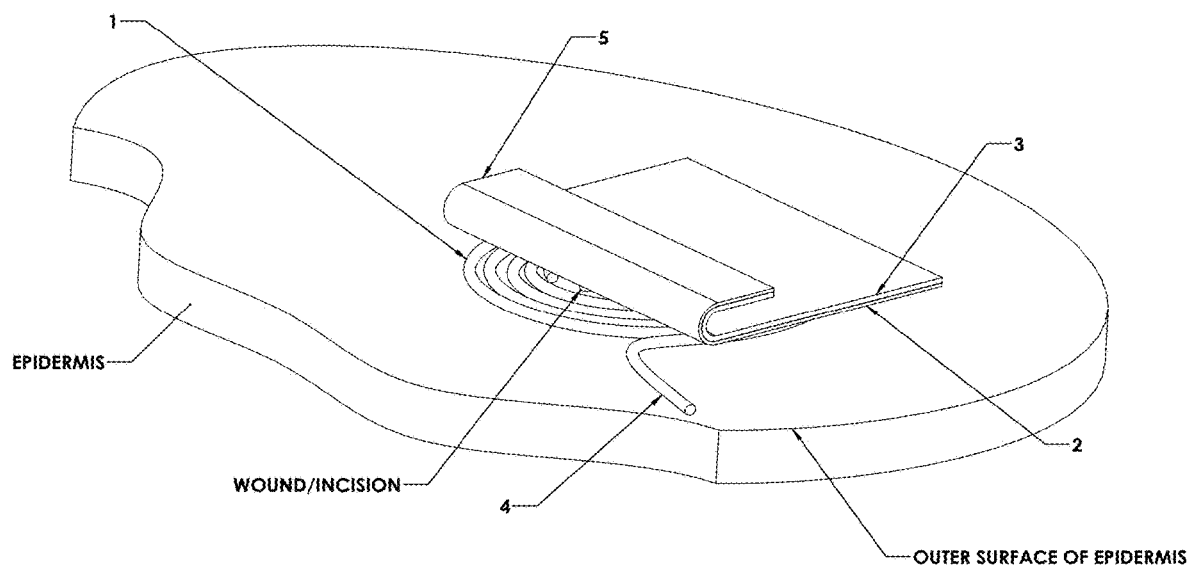
FIG. 5—Illustration of third embodiment whereby composite intermediate layer material affixed to the stringlike member.

A third embodiment of this disclosure is shown in FIG. 5 wherein the improved dressing/bandage includes intermediate layer 2, which preferably is a transparent/translucent membrane which includes at point of purchase stringlike or ribbonlike member 1 affixed to it by means of suitable gel/adhesive (not shown). Member 1 is preformed into a spiral or serpentine shape of any conceivable form as disclosed above and before being affixed to intermediate layer 2. The distribution of the gel/adhesive by the manufacturer may be contiguous uniform, contiguous but of varying localized pull-away strength or interrupted, the choice of which distribution affords it being pulled from the patient's skin in the desired atraumatic fashion. Once the assembly made up of 1 and 2 is affixed to the patient's skin self-stick dressing 3 of any desired characteristic can be applied over it. In this embodiment tail 4 is an optional feature of stringlike member 1 as the entire dressing may be removed atraumatically from the patient's skin by simply pulling back the composite member 2 and 3 with tab 5 in FIG. 5.

A fourth and preferred embodiment of this disclosure is seen in FIG. 6A wherein the spiral or serpentine form or stringlike member is not present as a distinct, physical object. Instead dressing/bandage 1 itself is debossed or perforated at time of manufacture to create a spiral or serpentine stringlike member to significantly reduce the peel away shear strength of the dressing/skin joint in a predetermined and precalculated manner. The debossing 2 in FIG. 6A is preferably of a serpentine, multi-turn, or spiral geometry form so as to leave ribbons of parent material between each debossed turn of the debossed spiral. It should be noted that debossing 2 may be partial in nature in terms of depth of cut or cut fully through the material 1 with perforations in FIG. 6A. Outer ribbon 3 in FIG. 6A is being pulled back to begin the spiral removal from the patient's epidermis with an expanded view of this action in FIG. 6B.

Figures 7, 7A, 7B:
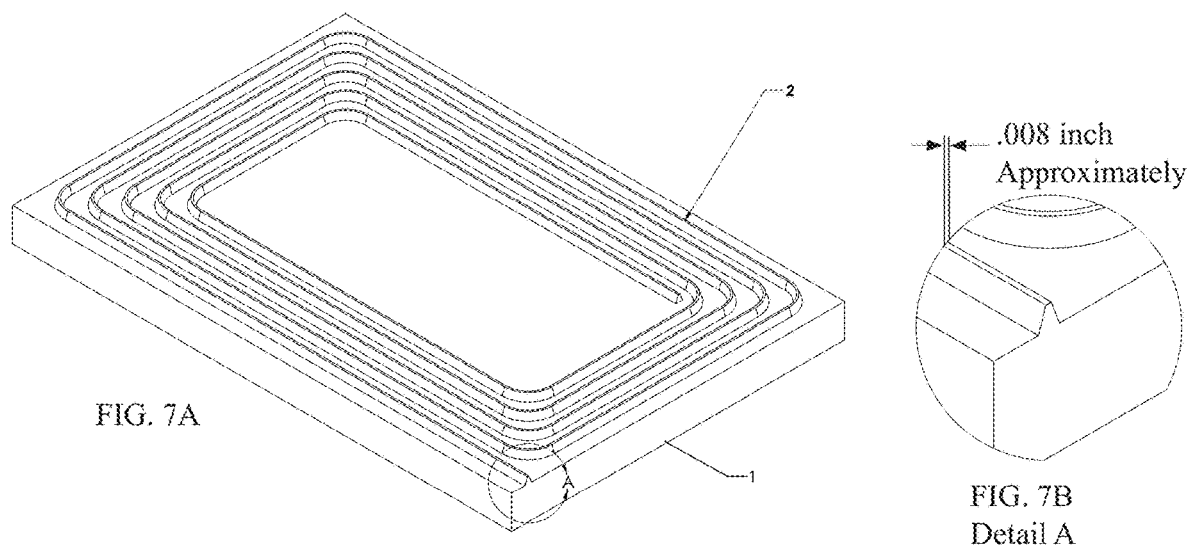
FIG. 7—Illustration of prototype for die-cutting or debossing stringlike pattern into dressing.

FIG. 7A shows a form of a male, debossing die 1 that may be utilized to create in manufacturing claimed article The debossing or die cut perforations 2 facilitate the atraumatic removal of the patch from the skin in the preferred fourth embodiment. This serpentine pattern of perforations in the patch is gained when the male die with unperforated bandage fabric is placed into a hydraulic or pneumatic press with suitable underlayment support comprised typically silicone rubber of a high Durometer hardness, and when (a) sufficient pressure is applied by virtue of the press, typically on the order of one ton and (b) serpentine ridges 2 in die 1 in FIG. 7A are of sufficient sharpness, typically but not limited to 0.008 inch in width as illustrated in FIG. 7B.

In summary, the physical characteristics for said improved spiral geometry bandage/dressing being deployed not only in wound care but for other purposes including but not limited to (a) patches applied to human skin and worn as a facilitator for breaking nicotine related human habit, (b) patches worn for pain management, (c) patches worn as muscle coverings in sportswear or athletic training such as but not limited to body building and track, and (d) any skin covering patch improved by virtue of the novel, physical said patches being deployed not only in human wound care but also in veterinary wound care and dermal therapies.

The invention claimed is:
1. An atraumatic dermal dressing comprising:
   a. a body comprising a wound/incision site region and a serpentine stringlike member region around the wound/incision site region,
   b. a serpentine stringlike member with multi-turn geometries formed by debossed ribbons of the body so as to reduce the peel away shear strength of the body, creating a smaller adhering surface at the incidence angle of pull upon the body's removal from the skin,
   c. a gel/adhesive on the skin-facing surface of the serpentine stringlike member so as to adhere the serpentine stringlike member to the skin, and
   d. a tail at the end of the outermost turn of the serpentine stringlike member to enable a user to pull the serpentine stringlike member and initiate the unwinding of the serpentine stringlike member and thus incrementally remove the body from the skin.

2. The atraumatic dermal dressing as in claim 1, wherein said body has a stiffness between about 5 Shore 00 and about 90 shore 00.

3. The atraumatic dermal dressing as in claim 1, wherein said body has a predetermined level of liquid porosity.

4. The atraumatic dermal dressing as in claim 1, wherein said serpentine stringlike member that originates on a predetermined distal boundary of said wound/incision site region.

5. The atraumatic dermal dressing as in claim 1, wherein said serpentine stringlike member terminates on a predetermined distal boundary of said body.

6. The atraumatic dermal dressing as in claim 1, wherein said serpentine stringlike member is comprised of a width between about 1 mm and about 25 mm.

7. The atraumatic dermal dressing as in claim 1, wherein said serpentine stringlike member is comprised of a predetermined thickness.

8. The atraumatic dermal dressing as in claim 1, wherein said serpentine stringlike member has a predetermined cross-sectional shape.

9. The atraumatic dermal dressing as in claim 1, wherein said debossed ribbons of the body are comprised of thicknesses between about 5 microns and about 250 microns.

10. The atraumatic dermal dressing as in claim 1, wherein said debossed ribbons of the body are comprised of a predetermined number of perforations.

11. The atraumatic dermal dressing as in claim 1, wherein said debossed ribbons of the body may vary in width between about 5 microns and about 3 mm.

12. The atraumatic dermal dressing as in claim 1, wherein said gel/adhesive has a coating weight between about 10 grams/m2 to about 70 grams/m2.

13. The atraumatic dermal dressing as in claim 1, wherein said gel/adhesive has predetermined surface tack characteristics.

* * * * *